United States Patent [19]

Shimatani et al.

[11] Patent Number: 5,270,462
[45] Date of Patent: Dec. 14, 1993

[54] PROCESS FOR MANUFACTURING SIALIC ACIDS-CONTAINING COMPOSITION

[75] Inventors: Masaharu Shimatani, Sayama; Yukio Uchida, Tokorozawa; Ichirou Matsuno, Kawagoe; Makoto Oyoshi; Yumiko Ishiyama, both of Sayama, all of Japan

[73] Assignee: Snow Brand Milk Products Co., Ltd., Hokkaido, Japan

[21] Appl. No.: 820,277

[22] Filed: Jan. 14, 1992

[30] Foreign Application Priority Data

Jan. 21, 1991 [JP] Japan .................................. 3-19113

[51] Int. Cl.$^5$ .............................................. A23C 9/142
[52] U.S. Cl. .................................... 536/17.2; 536/124; 426/40; 426/41; 426/42; 426/801; 530/366
[58] Field of Search ................. 536/17.2, 124; 426/41, 426/801, 40, 42; 530/366

[56] References Cited

U.S. PATENT DOCUMENTS

| | | | |
|---|---|---|---|
| 2,555,211 | 5/1951 | Wallace | 530/366 |
| 2,555,213 | 5/1951 | Wallace et al. | 530/366 |
| 3,073,747 | 1/1963 | Reid | 530/366 |
| 3,423,208 | 1/1969 | Kuipers | 530/366 |
| 3,862,901 | 1/1975 | Wennerblom et al. | 530/416 |
| 3,969,337 | 7/1976 | Lauer et al. | 530/366 |
| 4,018,752 | 4/1977 | Buhler et al. | 530/366 |
| 4,042,575 | 8/1977 | Eustache | 530/366 |
| 4,159,350 | 6/1979 | Jonsson | 426/271 |
| 4,229,342 | 10/1980 | Mirabel | 530/366 |
| 4,352,828 | 10/1982 | Riallano et al. | 530/366 |
| 4,436,658 | 3/1984 | Peyrouset et al. | 530/366 |
| 4,478,855 | 10/1984 | Dahlen et al. | 426/599 |
| 4,485,040 | 11/1984 | Roger et al. | 530/366 |
| 4,624,804 | 11/1986 | Voelter et al. | 530/366 |
| 4,782,138 | 11/1988 | Rialland et al. | 530/366 |
| 4,791,193 | 12/1988 | Okonogi et al. | 530/366 |
| 4,803,089 | 2/1989 | Chaveron et al. | 426/583 |
| 4,955,363 | 9/1990 | Harju et al. | 530/366 |
| 5,008,376 | 4/1991 | Bottomley | 530/366 |
| 5,061,622 | 10/1991 | Dosako et al. | 426/40 |
| 5,075,424 | 12/1991 | Tanimoto et al. | 530/361 |
| 5,149,647 | 9/1992 | Burling | 530/366 |

FOREIGN PATENT DOCUMENTS

| | | |
|---|---|---|
| 320152 | 6/1989 | European Pat. Off. . |
| 2443867 | 8/1980 | France . |
| 2179947 | 3/1987 | United Kingdom . |

OTHER PUBLICATIONS

Journal of the American Chemical Society, vol. 75, pp. 328-330 (1953).

*Primary Examiner*—Ronald W. Griffin
*Attorney, Agent, or Firm*—Seed and Berry

[57] ABSTRACT

The present invention relates to a process for manufacturing a composition containing sialic acids. The process of the present invention comprises the steps of: (a) adjusting cheese whey or rennet whey to a pH of 2-5; (b) contacting the whey with a cation exchanger, to produce an exchanger-passed solution; (c) adjusting the pH of the exchanger-passed solution to a pH of 4 or lower; and then (d) concentrating and/or desalting the exchanger-passed solution. According to the present invention, it is possible to produce a composition having a high sialic acids content at a low cost and in a simple and easy manner on an industrial scale. The high sialic acids content composition thus produced can be utilized as food materials or medical materials and therefore is very useful, industrially.

6 Claims, No Drawings

PROCESS FOR MANUFACTURING SIALIC ACIDS-CONTAINING COMPOSITION

DESCRIPTION

1. Technical Field

The present invention relates to a process for manufacturing a composition highly containing sialic acids from milk whey.

2. Background of the Invention

It is well known that sialic acids contained in milk whey include sialic acid-bound oligosaccharides such as sialyl lactose (hereinafter referred to as "SL") wherein sialic acid binds saccharides, κ-casein glycomacropeptide (hereinafter referred to as "GMP") wherein sialic acid binds peptides, gangliosides wherein sialic acid binds lipids, and so on. GMP is a sialic acid-bound peptide which forms when κ-casein of milk is subjected to rennet or pepsine and which is contained in cheese whey or rennet-casein whey.

Recently, it was known that saccharide chains contained in complex saccharides such as glycoproteins or glycolipids play an important role in intercellular recognition in a living body. It has begun to be recognized that sialic acid is particulary important as a constituent indispensable for a receptor associated with the intercellular recognition. Sialic acids are contained in breast milk in an amount of about 3-5 times that of milk and is considered to function as one of factors preventing infection in infants. In particular, it has become known that GMP prevents colon bacilli from adhering to intestinal tract cells; prevents infection with influenza virus (Japanese Unexamined Patent Published Application (hereinafter referred to as "J. P. Kokai") Sho No. 63-284133); reduces appetite (Bulletin of Experimental Biology and Medicine 96, 889 (1983)). Therefore, it has been strongly demanded that sialic acid should be industrially produced as a substituent for breast milk, as food such as functional food, and for medical materials.

Up to this date, as a technique for fractionating sialic acids contained in milk, there have been proposed a process for preparing sialic acid-bound proteins as disclosed in Japanese Patent Publication for opposition Purposes (hereinafter referred to as "J. P. Kokoku") Sho No. 40-21234, a process for preparing sialic acid-bound oligosaccharides as described in J. P. Kokai Sho No. 59-184197 and a process for preparing sialic acid-bound peptides (GMP) as described in J. P. Kokai Sho No. 63-284199. However, these processes are complex for industrial usage and have defects in economical point of view, for example, in that they need high costs for facilities and operation.

SUMMARY OF THE INVENTION

The object of the present invention is to provide a process for efficiently separating sialic acids from cheese whey or rennet casein whey on an industrial scale.

The present inventors have made intensive studies in order to attain the above object and have found that this object can be attained by adjusting to an acidic pH, cheese whey or rennet casein whey which contains sialic acids, by contacting the whey with a cation exchanger to form a solution which has passed through the cation exchanger (hereinafter referred to as "exchanger-passed solution") and recovering the exchanger-passed solution as a sialic acids-containing composition. In case where the exchanger-passed solution contains much lactose, it is preferable that the exchanger-passed solution be concentrated and crystallized to remove lactose. Further preferably, the exchanger-passed solution is concentrated and/or desalted and, if necessary, dried and changed into powder. Further, it is preferable that the exchanger-passed solution and/or a mother liquor after lactose has been removed therefrom be adjusted to a pH 4 or higher and then ultrafiltrated using an ultrafiltration membrane having a cutoff molecular weight of 2,000 to 50,000 Dalton, to remove lactose and ash content, while enhancing the content of sialic acids.

DETAILED EXPLANATION OF THE INVENTION

Whey containing sialic acids, the starting material of the present invention, is a by-product obtained when cheese or rennet casein is produced from milks such as cow milk, goat milk and sheep milk. Because a small amount of curd or fat often remains in milk whey, it is preferable that they be previously removed by a cream separator or clarifier. In order for milk whey proteins such as β-lactoglobulin to be efficiently adsorbed to a cation exchanger, the whey may be previously concentrated with an ultrafilteration device. Further, the whey may be previously desalted with an electric dializer and/or an ion exchange resin.

The whey is adjusted to a pH of 2-5 before it is subjected to the cation exchanger. As materials for adjusting the pH, any kind of materials may be used. For example, they include an acid such as hydrochloric acid, sulfuric acid, acetic acid, tactic acid and citric acid. Alternatively, acidified whey which has been desalted with the resin to have a pH of about 1-4, may be used for adjusting the pH, in order that the whey contains a high content of sialic acids. In the whey which has been adjusted to a pH of 2-5, sialic acids are negatively charged, while most part of whey protein is positively charged. When this whey is contacted with the cation exchanger, whey protein is selectively adsorbed to the cation exchanger and, as a result, sialic acids are selectively recovered as an exchanger-passed solution. If the pH of the whey is higher than 5, sialic acids and most part of whey protein are negatively charged. Therefore, the separation is not efficient, although these two can be separated with an anion exchanger utilizing difference in adsorption. If the pH of the whey is lower than 2, sialic acids decompose and therefore the process is not practical.

As techniques for causing whey protein to be adsorbed to an ion exchanger, there are known techniques such as those as described by J. N. de Wit et al.(Neth. Milk Dairy J., 40:41-56 (1986)) and J. S. Ayers et al.- (New Zealand J. Dairy Sci. and Tech., 21:21-35 (1986)), as well as those processes as described in J. P. Kokai Sho No. 52-151200 and 63-39545, and J. P. Kokai Hei No. 2-104246 and 2-138295. These techniques use a cation exchanger having an ion exchanger such as a carboxymethyl group or a sulfonate group and an anion exchanger having an ion exchanger group such as a quaternary methylammonium group (QMA). These techniques are merely employed to prepare whey protein isolate (WPI) by causing whey protein to be adsorbed to the ion exchanger. On the other hand, in these techniques, there is no consideration for efficient utilization of the exchanger-passed solution. The present inventors have paid attention to sialic acids contained in whey and found out a process for efficiently recovering sialic acids at a high concentration using a cation exchanger. The exchanger-passed solution thus obtained can be used as a high sialic acids content composition as it is. Alternatively, the solution may be used after it is concentrated and/or desalted or, if necessary, after dried and changed into powder. In addition, a mother liquor obtained after the exchanger-passed solution is concentrated and then crystallized to remove lactose may be used as a material having a high content of sialic acids. The concentration may be made by an evaporator. The crystallization may be made by cooling or by addition of a seed crystal.

In order to obtain a much higher sialic acids content composition, it is preferable that the pH of the exchanger-passed solution and/or its mother liquor be adjusted before they are concentrated and/or desalted. The concentration may be made by evaporation or by ultrafiltration. The desalting may be made by electric dialysis, ion exchange, ultrafiltration or diafiltration. The diafiltration is a technique for further increasing the protein content, wherein a liquid, which has been concentrated to some extent, is ultrafiltrated while simultaneously water is added thereto and a passing solution is withdrawn. When the exchanger-passed solution and/or its mother liquor is adjusted to a pH of 4 or higher, the concentration may be made by ultrafiltration using an ultrafiltration membrane having a cutoff molecular weight of 2,000~50,000 Dalton. The concentration may be also made by the ultrafiltration using an ultrafiltation membrane having a cutoff molecular weight of 10,000 at a pH of 4 or lower. In other words, $\kappa$-casein glycomacropeptide (GMP) as a sialic acid is present as a monomer at a pH of 4 or lower, while it associates into a multimonomer at a pH of above 4. As materials for adjusting the pH, any kind of materials may be used. They include alkalis such as sodium hydroxide, potassium hydroxide, calcium hydroxide, potassium carbonate, sodium citrate, etc.

The concentrate thus obtained is a composition having a high content of sialic acids such as GMP. Incidentally, $\alpha$-lactalubmin, which is usually contained in milk whey together with sialic acids, may be separated from sialic acids, for example, by ultrafiltering the exchanger-passed solution or its mother liquor at a PH of 4 or higher using an ultrafiltration membrane having a cutoff molecular weight of 2,000 to 50,000 Dalton.

According to the present invention, it is possible to produce a composition having a high sialic acids content at a low cost and in a simple and easy manner on an industrial scale, by contacting milk whey with a cation exchanger after the pH of the whey is adjusted. The high sialic acids content composition thus produced can be utilized as food materials or medical materials and therefore is very useful, industrially.

EXAMPLES

The present invention will be further illustrated in detail by reference to the following non-limitative examples.

REFERENCE EXAMPLE 1

100 kg of Cheddar cheese whey, which had been adjusted to a pH of 3.5 by hydrochloric acid, was mixed with 3 liters of Indion S3 (Phoenix Chemicals) as a cation exchanger, slowly stirred for 20 hours, and then separated with a filter into an exchanger-passed solution and the cation exchanger. The exchanger-passed solution thus obtained (99.2 kg) contained 5.5 g/100 g of a solid content, 0.6 g/100 g of protein, and 20 mg/100 g of sialic acids. Sialic acids were quantitatively determined with EYELA CARBOXYLIC ACID ANALYZER S-14 (TOKYO RIKAKIKAI CO., LTD.) (reported by Naoki Ii of Analysis Dept. of Snow Brand Company on Mar. 29, 1990 at Nihon Shokuhin Kogyo Gakkai (Japan Food Society) 37th Meeting). The amounts of sialic acids is represented in terms of sialic acid which is measured by making sialic acid free from sialic acids, which are a mixture of sialyllactose and glycomacropeptide.

REFERENCE EXAMPLE 2

100 kg of rennet casein whey, which had been adjusted to a pH of 4.0 with hydrochloric acid, was passed through a column filled with 4 liters of CM-Sephadex C-50 (Pharmacia) as a cation exchanger at an SV of 2.5 for 10 hours. The exchanger-passed solution (99.0 kg) contained 5.8 g/100 g of a solid content, 0.4 g/100 g of protein, and 20 mg/100 g of sialic acids.

REFERENCE EXAMPLE 3

The exchanger-passed solution in Reference Example 1 was concentrated to a solid content of 60% using an evaporator and then crystallized to remove lactose. A mother liquor (6.4 kg) obtained after the crystallized lactose was washed with water contained 34.3 g/100 g of a solid content, 4.6 g/100 g of protein, and 300 mg/100 g of sialic acids.

EXAMPLE 1

The exchanger-passed solution obtained in Reference Example 1 was adjusted to a PH of 6.4 with sodium hydroxide, ultrafiltrated using an ultrafiltration membrane having a cutoff molecular weight of 20,000, and then desalted with diafiltration. The resultant desalted and concentrated solution (10 kg) contained 3.7 g/100 g of a solid content, 2.8 g/100 g of protein, and 150 mg/100 g of sialic acids. The solution was further concentrated and dried according to the conventional manner to yield 0.39 kg of powder.

EXAMPLE 2

5.6 kg of water was added to the mother liquor obtained in Reference Example 3. The resultant solution was adjusted to a pH of 6.0 with potassium carbonate and then ultrafiltrated using an ultrafiltration membrane having a cutoff molecular weight of 8,000 Dalton. The resultant concentrated solution was desalted by diafiltration. The resultant concentrated and desalted solution (12 kg) contained 3.1 g/100 g of a solid content, 2.3 g/100 g of protein, and 100 mg/100 g of sialic acids. The solution was further concentrated and dried according to the conventional manner to yield 390 g of powder.

EXAMPLE 3

The exchanger-passed solution obtained in Reference Example 2 was adjusted to a pH of 5.8 with sodium hydroxide and then ultrafiltrated using an ultrafiltration membrane having a cutoff molecular weight of 20,000 Dalton. The resultant concentrated solution was desalted by diafiltration. The resultant desalted and concentrated solution (10 kg) contained 6.2 g/100 g of a solid content, 3.8 g/100 g of protein, and 180 mg/100 g of sialic acids. The solution was further concentrated and dried according to the conventional manner to yield 0.645 g of powder.

EXAMPLE 4

The exchanger-passed solution obtained in Reference Example 2 was adjusted to a pH of 3.5 with hydrochloric acid and then ultrafiltrated using an ultrafiltration membrane having a cutoff molecular weight of 8,000 Dalton. The resultant concentrated solution was desalted by diafiltration. The resultant concentrated and desalted solution (10 kg) contained 6.1 g/100 g of a solid content, 3.7 g/100 g of protein, and 182 mg/100 g of sialic acids. The solution was further concentrated and dried according to the conventional manner to yield 0.640 g of powder.

EXAMPLE 5

A mixture of 5 kg of the exchanger-passed solution obtained in Reference Example 1 with 5 kg of the mother liquor obtained in Reference Example 3 was adjusted to a pH of 6.0 with potassium carbonate and then ultrafiltrated using an ultrafiltration membrane having a cutoff molecular weight of 8,000 Dalton. The resultant concentrated solution was desalted by diafiltration. The resultant desalted and concentrated solution (2.5 kg) contained 14 g/100 g of a solid content, 9 g/100 g of protein, and 480 mg/100 g of sialic acids. The solution was further concentrated and dried according to the conventional manner to yield 360 g of powder.

EXAMPLE 6

5.6 kg of water was added to the mother liquor obtained in Reference Example 3. The resultant solution was adjusted to a pH of 3.6 with HCl and then ultrafiltrated using an ultrafiltration membrane having a cutoff molecular weight of 8,000 Dalton. The resultant concentrated solution was desalted by diafiltration. The resultant concentrated and desalted solution (4 kg) contained 10.0 g/100 g of a solid content, 7.3 g/100 g of protein, and 475 mg/100 g of sialic acids. The solution was further concentrated and dried according to the conventional manner to yield 380 g of powder.

What is claimed is:

1. A process for recovering, from cheese whey or rennet whey, sialic acid-bound oligosaccharides, sialic acid-bound peptides and sialic acid-bound lipids at a high concentration, comprising the steps of:
   (a) adjusting cheese whey or rennet whey to a pH of 2-5;
   (b) contacting the whey with a cation exchanger, to produce an exchanger-passed solution; and
   (c) concentrating and/or desalting said exchanger-passed solution.

2. The process of claim 1, further comprising a step of drying and changing the exchanger-passed solution into powder after the step (c).

3. The process of claim 1, wherein in the step (c), if the exchanger-passed solution has a pH lower that 4, then adjusting the exchanger passed solution to a pH of 4 or higher, and desalting the exchanger-passed solution by diafiltration method using an ultrafiltration membrane having a cutoff molecular weight of 2,000-50,000 Dalton.

4. The process of claim 1, further comprising a step of concentrating and crystallizing the exchanger-passed solution after the step (b) and before the step (c), to remove lactose therefrom and yield a mother liquor.

5. The process of claim 4, further comprising a step of adding water to the mother liquor, to prepare the exchanger-passed solution in the step (c).

6. The process of claim 1, wherein in the step (c), if the exchanger-passed solution has a pH higher than 4, then adjusting the exchanger passed solution to a pH of 4 or lower, and desalting the exchanger-passed solution by diafiltration method using an ultrafiltration membrane having a cutoff molecular weight of 10,000 Dalton or lower.

* * * * *